(12) United States Patent
Kohn et al.

(10) Patent No.: US 8,632,735 B2
(45) Date of Patent: Jan. 21, 2014

(54) SYSTEM AND METHOD FOR TITRATING LIQUIDS

(75) Inventors: Heinz-Gerhard Kohn, Hamburg (DE); Karl-Friedrich Andres, Hamburg (DE)

(73) Assignee: Eppendorf AG, Hamburg (DE)

( * ) Notice: Subject to any disclaimer, the term of this patent is extended or adjusted under 35 U.S.C. 154(b) by 1440 days.

(21) Appl. No.: 11/624,303

(22) Filed: Jan. 18, 2007

(65) Prior Publication Data
US 2007/0203457 A1 Aug. 30, 2007

(30) Foreign Application Priority Data
Feb. 28, 2006 (DE) .......................... 10 2006 009 816

(51) Int. Cl.
*A61M 5/00* (2006.01)
(52) U.S. Cl.
USPC ........... 422/509; 422/501; 422/514; 422/515; 422/516; 422/517; 422/518; 422/519; 422/520; 422/521; 422/524; 422/565; 422/919; 422/922; 422/925; 422/926; 422/927; 422/928; 422/929; 436/180; 73/1.74; 73/863.32; 73/864.01
(58) Field of Classification Search
USPC ......... 422/501, 514–521, 524, 565, 919, 922, 422/925–929; 436/180
See application file for complete search history.

(56) References Cited

U.S. PATENT DOCUMENTS

| | | | |
|---|---|---|---|
| 2,966,175 A * | 12/1960 | Hyde | 141/27 |
| 4,058,365 A | 11/1977 | Krogh | |
| 4,563,907 A | 1/1986 | Johnson, Jr. et al. | |
| 4,671,123 A * | 6/1987 | Magnussen et al. | 73/864.16 |
| 4,821,586 A | 4/1989 | Scordato et al. | |
| 5,002,737 A | 3/1991 | Tervamaki | |
| 7,574,929 B2 * | 8/2009 | Telimaa et al. | 73/864.16 |
| 7,694,592 B2 * | 4/2010 | Molitor et al. | 73/864.18 |
| 2003/0099578 A1 | 5/2003 | Cote | |
| 2008/0034898 A1 * | 2/2008 | Molitor et al. | 73/864.16 |

FOREIGN PATENT DOCUMENTS

| | | |
|---|---|---|
| DE | 267331 | 3/1912 |
| DE | 26 17 346 | 4/1976 |
| DE | 0 691 158 B1 | 6/1995 |
| DE | 197 23 852 A1 | 10/1998 |
| EP | 0 576 967 A2 | 6/1993 |
| EP | 0 656 229 B1 | 10/1994 |
| EP | 0 657 216 B1 | 10/1994 |
| EP | 10 2005 023 203 A1 | 11/2006 |

\* cited by examiner

*Primary Examiner* — Brian R Gordon
*Assistant Examiner* — Shogo Sasaki
(74) *Attorney, Agent, or Firm* — Vidas, Arrett & Steinkruas

(57) ABSTRACT

A system for titrating liquids, with a syringe or tip, comprising a holding device and at least one tag and a metering equipment, comprising an additional holding device for holding the syringe or tip on the holding device, a reading device for reading the tag of the syringe or tip held by the additional holding device, a driving device having a motor, which is detachably coupled with a plunger of the syringe when the same is held by the additional holding device, or which is coupled with a plunger which is arranged in a cylinder which is coupled with the tip via a fluid conduit, when the same is held by the additional holding device, an operating device for operating the metering equipment and a control device, connected with the operating device, the reading device and the driving device, which controls the movement of the plunger depending of the tag of the inserted syringe or tip.

26 Claims, 1 Drawing Sheet

SYSTEM AND METHOD FOR TITRATING LIQUIDS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The titrimetric analysis or titrimetry is a determination method of the chemical analytics, in which the dissolved substance to be determined (the titrant or solution to be titrated) is reacted with an other substance of known concentration (the titrans, titration liquid, standardized solution), also mostly in a dissolved state, up to an end point, equivalency point or apex point (called hereinafter "end point" in a summarizing manner). The determination procedure is called titration. The end point is indicated by an indicator system, for instance, or in an electrochemical way or by means of a precipitation reaction.

For measuring the standardized solution, the burette is conventionally used. Further known is a metering system which is applicable to titration purposes. The latter has a metering equipment realised as a hand-held instrument, into which a syringe for the pick-up and delivery of liquids is insertable. For the instrumentation of the metering equipment, there are syringes with different nominal volumes. The metering system is switchable into a titration mode, which is characterised in that the speed of the syringe plunger or the delivered mass flow is decreased automatically about one level at each delivery step, in order to make more precise titration possible. Finally, the speed remains constant at the lowermost level.

In the titration systems up to now, there is the danger that too much liquid can be delivered in the region of the end point upon unintended wrong procedure. Even when a small mass flow is delivered in the proximity of the end point with the known metering system, it may happen that the end point is missed. For instance, reaching the end point is recognised too late because titrant and titrans do not mix homogeneously and react with each other instantly. Furthermore, the user needs a reaction time from recognising the end point up to releasing the triggering button, during which further titrans flows in and the end point can be exceeded. When using the metering equipment with syringes having different nominal volumes, the delivered mass flows can be very different in a certain delivery step. Use of different syringes may also complicate the determination of the end point.

If the end point is missed in the context of a pH-value adjustment for an unbuffered or weakly buffered solution, the expense for correction may be very time-consuming. It is also possible that corrections lead to a dilution of the component(s) of interest in the solution to be processed, which is too high for the following working steps. In this case, the titrated solution has to be discarded. If the end point is exceeded in an analytic goal, the probable end point can be sometimes found by interpolation. When this is not possible or not allowed for procedural regulations, the titration has to be repeated with an additional sample.

Departing from this, the present invention is based on the objective to provide a system and method for titration which makes it possible to facilitate the recognition of the end point of the titration.

BRIEF SUMMARY OF THE INVENTION

The system for titrating liquids has a syringe or tip, comprising a holding device and at least one tag and a metering equipment, comprising an additional holding device for holding the syringe or tip on the holding device, a reading device for reading the tag of the syringe or tip held by the additional holding device, a driving device having a motor, which is detachably coupled with a plunger of the syringe when the same is held by the additional holding device, or which is coupled with a plunger which is arranged in a cylinder which is coupled with the tip via a fluid conduit, when the same is held by the additional holding device, an operating device for operating the metering equipment and a control device, connected with the operating device, the reading device and the driving device, which controls the movement of the plunger depending of the tag of the inserted syringe or tip.

The system according to the present invention has a syringe or tip and a metering equipment.

The syringe comprises a cylinder and a plunger movable therein, the cylinder having a passage opening for sample liquid. With the tip it is dealt with a small pipe, which can be completely or partially realised to be cylindrical or conical in particular, and which has a passage opening for sample liquid on one end and a passage opening for air on the other end The syringe or tip has at least one tag, which contains an information regarding the respective type and/or condition of the syringe or tip, for instance. For instance, the information is related to the nominal volume and/or the construction type (shape and/or dimensions, for instance) and/or the material and/or the purity grade and/or the manufacturer and/or the manufacturing date and/or carried out usages of the syringe or tip. The metering equipment has a reading device which is capable to read the tag of the syringe or tip, when the latter is held on the metering equipment by the additional holding device. The control device controls the movement of the plunger depending on the actuation of the operating device and of the tag read by the reading device.

As a consequence, it is possible to adapt the movement of the plunger to the type and/or the condition of the respective inserted syringe or tip. For instance, the speed and/or the acceleration and/or the displacement of the plunger (i.e. the path passed over by the plunger) can be matched to the respective syringe or tip. In particular, as a result the delivered mass flows can be matched to the respective syringe or tip. For instance, the mass flows delivered in a certain delivery step can be equal at syringes or tips of different nominal volumes, which facilitates titrating with syringes or tips having different nominal volumes for the user. Further, it is possible to deliver small defined amounts of liquid (droplets for instance) independent of the respective used syringe or tip at the end of the titration. The delivery of small defined amounts of liquid facilitates the recognition of the end point for the user. Errors due to a reaction time of the user can be avoided. The delivery of small defined amounts of liquid is explained in more detail below. Thus, the system facilitates reaching the end point of the titration for the user. Infringements of the detection of the end point of a titration due to the use of different syringes or tips do not take place.

The tag can be realised in many different ways. In particular, arbitrary realisations come into consideration, which can be acquired by means of sensors or measurement data pickups. For instance, the tag comprises a microchip and/or a RFID, into which data are written and/or writable which can be read by the reading device.

According to one embodiment, the tag can be sensed mechanically and/or optically. In this, it is dealt with elevations or deepenings of a plane of the syringe or tip, which can be sensed mechanically and/or optically The specific arrangement of the elevations and/or deepenings forms the tag of the respective syringe or tip. According to a further embodiment, the reading device is a device for mechanical and/or optical sensing. The reading device is apt to sense the tag which can be sensed mechanically and/or optically. In particular; the tag and the reading device can be formed like the sensing planes and the sensing device according to EP 0 657 3 16 B1, the entire contents is incorporated herein by reference, the disclosure relating to this being incorporated by reference into the present application.

In principle, the tag can be disposed on arbitrary positions of the syringe or tip According to one embodiment, it is disposed on a flange of the syringe or tip and/or on a plunger of the syringe For instance, elevations and/or deepenings are disposed circulating on the top of a flange, as has been described in EP 0 657 216 B1, the entire contents of which is incorporated herein by reference. According to another example, the tag is formed by circulating beads and/or grooves on a portion of the plunger projecting out of the cylinder.

The movement of the plunger can be influenced in different ways, depending on the individual syringe or tip. According to one embodiment, the control device controls a lower speed and/or a lower acceleration and/or a smaller displacement of the plunger at syringes or tips with greater volume than at syringes or tips with smaller volume. This makes it possible for the user to work with smaller material flows of delivered liquid even at greater syringes, which correspond to the material flows of smaller syringes or tips. According to another embodiment, the control device controls a higher speed and/or a higher acceleration and/or a greater displacement of the plunger at syringes or tips with greater volume than at syringes or tips with smaller volume. This can make sense, for instance, in order to form drops with greater syringes. Combinations of the aforementioned embodiments are also possible, which for instance enable equal material flows of delivered liquid as do smaller syringes or tips, with syringes or tips having a greater nominal volume in some distance from the end point through smaller speed of the plunger, but enable the delivery of droplets in the proximity of the end point through faster or more accelerated or greater movement, respectively, of the plunger.

In principle, the system may be realised as a pure titration system. According to one embodiment, the control device is switchable into a into a titration mode and/or into a dispensing mode and/or into a pipetting mode and/or into an aspiration mode and/or into a sequential dispensing mode. The system of that kind is capable to work in different operating modes. In the dispensing mode, the picked-up liquid is stepwise delivered in equal partial volumes. Every step can be individually triggered by the user through actuation of the actuating device. But automatic metering is also possible, in which single amounts of liquid are repeatedly delivered automatically upon one actuation of the operating device. In the pipetting mode, a picked-up amount of liquid is metered in one step. In the aspiration mode, a defined volume is picked up one after the other several times. The aspiration mode takes place approximately reversely to the dispensing mode In the sequential dispensing mode, several different dispensing volumes are delivered. In this, realisations are possible in which a variety of different dispensing volumes can be defined differently.

The system for titrating liquids has a syringe or tip, comprising a holding device and a metering equipment, comprising an additional holding device for holding the syringe or tip on the holding device, a driving device having a motor, which is detachably coupled with a plunger of the syringe when the same is held by the additional holding device, or which is coupled with a plunger which is arranged in a cylinder which is coupled with the tip via a fluid conduit, when the same is held by the additional holding device, an operating device for operating the metering equipment and a control device, connected with the operating device and the driving device, which controls a movement of the plunger for the delivery of big amounts of liquid in a first delivery phase and controls a movement of the plunger for the delivery of at least one small defined amount of liquid in a second delivery phase when triggered by an actuation of the operating device or by reaching the end of the first delivery phase.

The system according to the present invention has a syringe or tip and a metering equipment.

The syringe comprises a cylinder and a plunger movable therein, the cylinder having a passage opening for sample liquid. With the tip it is dealt with a small pipe, which can be completely or partially realised to be cylindrical or conical in particular, and which has a passage opening for sample liquid on one end and a passage opening for air on the other end. The metering device has a control device, which controls a movement of the plunger for the delivery of big amounts of liquid in a first delivery phase and controls a movement of the plunger for the delivery of at least one small defined amount of liquid in a second delivery phase. As a consequence, the end point can be roughly approached in the first delivery phase and can be accurately reached in the second delivery phase. The delivery of small defined amounts in the second delivery phase favours the accurate detection of the end point and avoids exceeding the end point due to a reaction time. As a consequence, the user can find the end point more easily.

The small defined amounts of liquid can have a volume in a wide range. According to a further embodiment, the control device controls the delivery of small defined amounts of liquid having a volume smaller than $1/100$ of the nominal volume of the syringe or tip. According to a further embodiment, the control device controls the delivery of small defined amounts of liquid having a volume smaller than $1/500$ of the nominal volume of the syringe or tip. According to a further embodiment, the control device controls the delivery of small defined amounts of liquid having a volume in the region of about one or several thousandths of the nominal volume of the syringe or tip Further, the delivery of the small defined amounts of liquid is possible in different ways. According to one embodiment, the control device controls the delivery of small defined amounts of liquid in a free jet. This is particularly advantageous for avoiding contaminations by contact of the syringe or tip with a vessel and/or for the delivery of very small droplet sizes. According to another embodiment, the control device controls the delivery of small defined amounts of liquid in the form of a running off flow. The delivery of small defined amounts of liquid in the form of a flow running off from the passage opening of a syringe or tip is advantageous in applications, for instance, in which guiding of the syringe or tip on the edge of a vessel is desired, in order to exactly hit the interior of the vessel. According to a further embodiment, the control device is switchable into a mode for the delivery of small defined amounts of liquid in a free jet and into a mode for the delivery of small defined amounts of liquid in the form of a running off flow through actuation of the actuating device.

According to one embodiment, the control device controls the delivery of small defined amounts of liquid in the form of droplets. The droplets are ejected from the syringe or tip, for instance, and/or run off from the syringe or tip, depending on the realisation of the control device. According to one embodiment, the control device can be switched from an operating mode in which droplets are ejected and an operating mode in which droplets run off.

The movement of the plunger in the first delivery phase can be controlled in different ways. According to one embodiment, the control device controls the movement of the plunger in the first delivery phase when an operating element of the operating device is actuated, and the rest of the plunger when the operating element is not actuated. As a consequence, liquid is delivered in the first delivery phase as long as the user actuates the operating element. According to a further embodiment, the control device reduces the speed of the plunger with respect to its speed at the preceding actuation at every subsequent actuation of the operating element. Through this, delivery steps are made possible in which the mass flow of the liquid to be delivered decreases with each step.

According to another embodiment, the control device controls a movement of the plunger in the first delivery phase such that upon each actuation of the actuating device, a large defined amount of liquid is delivered.

The second delivery phase can be initiated in different ways. According to one embodiment, the control device controls a movement of the plunger only for a predetermined number of actuations of the operating element, and initiates the second delivery phase when the maximum number has been reached. According to a further embodiment, the control device initiates the second delivery phase upon a defined actuation of the operating device. The two embodiments can also be combined with each other, so that the user can initiate the second delivery phase in every desired moment.

According to a further embodiment, the control device is connected with a sensor, which aims at a volume to which the delivery opening of a syringe or tip is directed when it is held by the additional holding device on the metering equipment, in order to detect an approach to the apex point of the titration, and the control device reduces the speed of the plunger and/or initiates the second delivery phase when approaching the apex point of the titration in the first delivery phase. In this embodiment, the speed of the plunger in the first delivery phase is automatically controlled and/or the second delivery phase is automatically initiated, for instance when the sensor detects a colour changeover of an indicator system and/or a change of the conductivity and/or a precipitation reaction. This embodiment can be combined with at least one of the two preceding embodiments for initiating the second delivery phase, so that the user can choose between different possibilities for initiating the second delivery phase.

In both resolutions and their embodiments, the holding device and the additional holding device can be realised differently. According to one embodiment, the holding device is realised like the fixation portion and the additional holding device is realised like the gripping devices of the pipette system according to EP 0 656 229 B1, the entire contents of which is incorporated herein by reference, the expositions of which relating to these topics are incorporated into the present application by reference.

According to one embodiment, the holding device comprises a flange on a cylindrical or sleeve-shaped body of the syringe or tip and/or a collar at the end of a plunger of the syringe.

According to a further embodiment, the additional holding comprises a plug-in receptacle of the metering equipment and at least one gripper, which is movable from a position releasing the holding device to a position capturing the holding device in the plug-in receptacle.

The driving device can have different motors. Realisations with pneumatic or hydraulic motors are possible, for instance. According to one embodiment, the driving device has an electric motor. The electric motor can be of different constructions. According to one embodiment, the electric motor is a DC motor.

According to one embodiment, the control device establishes the amount of liquid that has been delivered. The overall amount of liquid delivered in the first delivery phase can be established by summing up the big amounts of liquid delivered in every step. The overall amount of liquid delivered in the second delivery phase can be established by counting the small defined amounts of liquid which were delivered.

Establishing delivered amounts of liquid can take place in different ways. For instance, establishing can take place in that a stepping motor is used as the motor and the control device detects the steps which the stepping motor carries out for displacing the plunger. By means of the steps and the step widths, the control device can establish the displacement of the plunger. According to one embodiment, the driving device and/or the plunger is coupled with an increment transmitter for detecting the position of the plunger, and the control device is coupled with a sensor for sensing the increment transmitter. By doing so, the actual displacement of the driving device and the plunger, respectively, is established and made the basis for establishing the delivered amount of liquid.

The operating device can be realised in different ways, pneumatic or hydraulic on-off valves being possible for instance, in combination with a pneumatic or hydraulic motor in particular. According to one embodiment, the operating device comprises at least one electric push-button and/or an electric switch.

Different realisations of the control device are possible, a pneumatic or hydraulic control device for instance, in combination with a pneumatic or hydraulic motor in particular According to one embodiment, the control device is an electric control device. According to a further embodiment, the control device is program driven. For instance, the control device has a microcomputer or microcontroller.

The method for titrating liquids comprises the following steps: a syringe or tip with at least one tag is detachably connected to a metering equipment, the metering equipment reads at least one tag from the syringe or tip and the metering equipment moves a plunger of the syringe or a plunger in a cylinder connected with the syringe depending on an input of the user.

According to one embodiment of the method, the metering equipment senses the tag mechanically and/or optically from the syringe or tip.

According to one embodiment of the method, the syringe or tip is provided with a tag relating to the nominal volume and/or the construction type and/or the material and/or the purity grade and/or the manufacturer and/or the manufacturing date and/or carried out usages of the syringe or tip.

According to one embodiment, the metering equipment controls the speed and/or the acceleration of the plunger and/or the displacement of the plunger when small amounts of liquid are delivered, depending on the tag of the syringe or tip which is set in.

According to one embodiment, one operating mode of the metering equipment is selected among one or plural of the operating modes titration mode, dispensing mode, pipetting mode, aspiration mode and sequential dispensing mode.

The method for titrating liquids comprises the following steps: a syringe or tip is detachably connected to a metering equipment, in a first delivery phase a plunger of the syringe or a plunger in a cylinder connected to the tip is moved for the delivery of large amounts of liquid, and the plunger is moved for the delivery of at least one small defined amount of liquid in a second delivery phase.

According to one embodiment, the plunger is moved upon actuation of an operating element and is stopped upon release of the operating element in the first delivery phase.

According to one embodiment, at every subsequent actuation of the operating element the speed of the plunger with respect to its speed at a preceding actuation is reduced in the first delivery phase.

According to one embodiment, the second delivery phase is initiated after a predetermined number of actuations of the operating element.

According to one embodiment, the second delivery phase is initiated after a special actuation of an operating element.

According to one embodiment, the solution with the substance to be determined is monitored and upon approaching the apex point of the titration, the speed of the plunger is reduced and/or the second delivery phase is initiated.

BRIEF DESCRIPTION OF THE SEVERAL VIEWS OF THE DRAWINGS

In the following, the present invention is explained in more detail by means of the attached drawings of examples of realisation. In the drawings show.

DETAILED DESCRIPTION OF THE INVENTION

Figure 1:
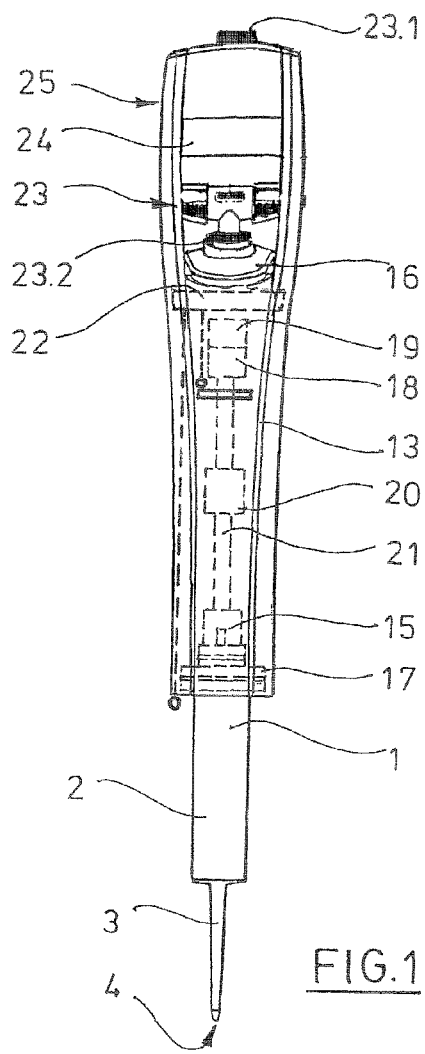
FIG. 1 a syringe with a metering device holding the same, in a front view.
Figure 2:
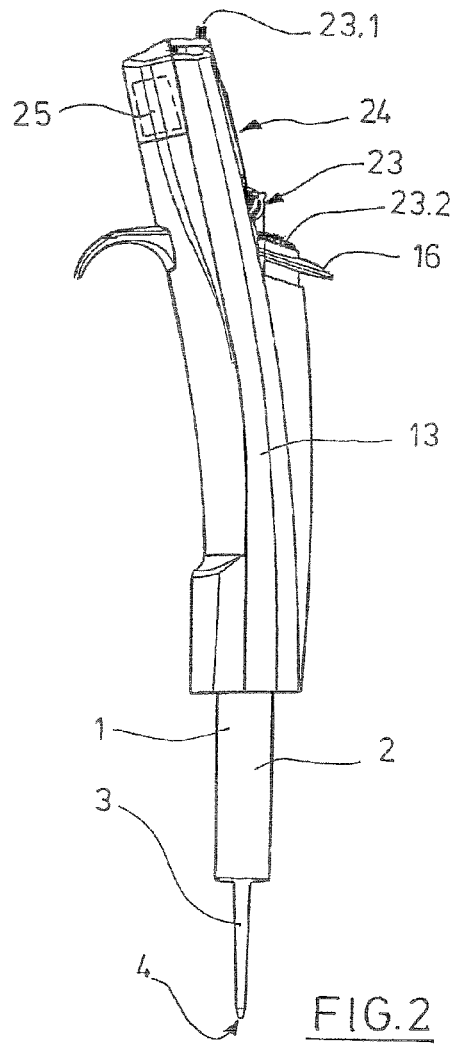
FIG. 2 the same syringe and the metering device holding the same, in a side view.
Figure 3:
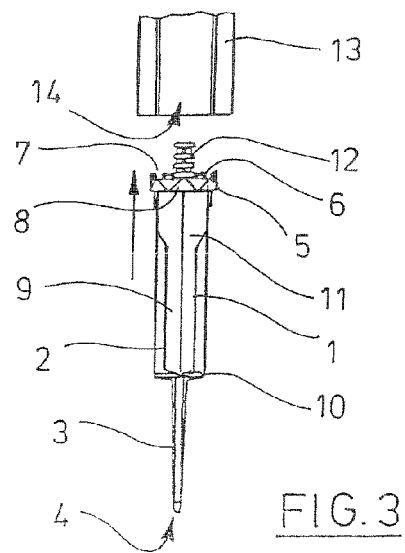
FIG. 3 the syringe when it is inserted into the lower part of the metering device, in a front view.

While this invention may be embodied in many different forms, there are described in detail herein a specific preferred embodiment of the invention. This description is an exemplification of the principles of the invention and is not intended to limit the invention to the particular embodiment illustrated.

A syringe 1 has a cylinder 2, which on its downside has a little pipe 3 with a passage opening 4 on the bottom end. On the top, the cylinder 2 has a flange 5 which has elevations 6 and deepenings 7. Through the special arrangement of the elevations 6 and deepenings 7, a tag of the syringe 1 is created which indicates the nominal volume thereof. On the outer perimeter of the flange 5, there are guiding grooves 8 in order to align the syringe 1 in certain angle positions in a receptacle.

In the interior of the syringe 1, a plunger 9 is disposed, which has a cylindrical or disc-shaped region 10 on its bottom, sealingly guided in the cylinder 2, and a plunger rod 11 connected therewith. The plunger rod 11 has circulating beads 12 on its topside, which serve for fixing the plunger 9 in a plunger accommodation.

A metering equipment 13 has a casing, which has a plug-in receptacle 14 for the flange of the syringe 1 at the bottom In the metering equipment 13, there is a displaceable plunger accommodation 15 for the plunger. The flange 5 and the plunger rod 11 of the plunger 9 are held in the metering equipment 13 by not shown gripping devices.

Details of the syringe 1 and of the further holding devices for holding the syringe 1 in the metering equipment 13 are described in EP 0 656 229 B1, to which is referred in so far.

Further, the metering equipment 13 has a discarding push-button 16, which makes it possible to release the holding device centrally Details of the central discarding installation for the syringe 1 are described in the German patent application 10 2005 0023 203.5, the expositions of which relating to these topics are incorporated into the present application by reference.

Further, the metering equipment comprises a reading device 17 for sensing the elevations 6 and deepenings 7. Details of the reading device 17 and of the tagging of the syringes 1 by elevations and deepenings are described in EP 0 657 216 B1, to which is reference made in so far.

The metering equipment 13 comprises a driving device 18 which has an electric motor 19. The electric motor 19 is coupled with the plunger accommodation 16 with a lifting rod 21 via a gear 20.

Further, the metering equipment 13 comprises an electronic control device 22. The same is electrically connected with the electric driving device 18. Further, it is connected with an operating device 23 and a display 24, which are situated in the upper region of the metering device 13. The operating device 23 comprises a shifting switch 23. 1 or the like for setting an operating mode of the metering device 13. The shifting switch permits a selection among the operating modes titrating, pipetting, dispensing, automatic dispensing, aspirating and sequential dispensing.

Further, the metering equipment 13 comprises an electric power supply 25 in the form of an accumulator. The accumulator can be charged by an external power supply.

In the titration mode, movement of the plunger 9 is possible with different speeds. At each actuation of a triggering push-button 23.2 of the metering device, the plunger 9 is controlled to have a slower speed. The speeds on each level depend of the nominal volume of the syringe 1, which is indicated to the control device by the reading device 17.

The example of realisation has ten different speeds for the movement of the plunger 9 when delivering liquid in the titration mode. After the smallest speed level has been reached, the delivery of a defined small amount of liquid in a free jet is triggered by further actuation of the triggering push-button 23.2. All together, the process of the pick-up and delivery of liquids in the titration mode can be represented as follows:

For the pick-up of liquid, the triggering push-button 23,2 is pushed shortly one time. The pick-up of liquid is stopped by a second actuation of the triggering push-button 23.2. If not, liquid corresponding to the nominal volume of the syringe 1 is automatically sucked up.

Thereafter, a further actuation of the triggering push-button 23.2 causes a small reverse stroke, which compensates a clearance between driving device 18 and plunger 9. In this, a small amount of the sucked-up liquid is discarded.

Upon further actuation of the triggering push-button, the plunger 9 is at first moved with maximum speed, as long as the triggering push-button 23.2 is kept pushed. Upon release of the triggering push-button 23.2, the plunger is stopped.

Repeated pressure on the triggering push-button 23.2 causes further movement of the plunger 9 with the second highest speed.

At each further release and actuation of the triggering push-button 23.2, a lower speed level is reached, until the plunger 9 is lowered with the slowest speed.

Thereafter, every further actuation of the triggering push-button 23.2 causes release of liquid in the form of droplets with great speed. The droplets have a volume which corresponds to about one thousandths of the nominal volume of the syringe 1. Further, by actuating the operating devices 23 it is possible to directly switch to the droplet-wise delivery of liquid from each speed level. Further, by suitable actuation of the operating device 23 an automatic droplet delivery is also possible, such that single droplets are delivered at certain time intervals.

In this, a delivery in droplet form is controlled by the short actuation of the triggering push-button 23.2, and by long-acting actuation of the triggering push-button 23.2 an advancement of the plunger 9 up to the stop on the bottom end of the cylinder 2. Thus, after reaching the end point, it is possible for the user to promptly discard the residual solution still contained in the syringe 1.

The display 24 shows the total delivered liquid volume which the control device 22 establishes. To establish the delivered volume of liquid, the movement of the electric motor 19 is acquired by a not shown arrangement of an increment transmitter and a sensor.

After the titration, the syringe 1 can be easily discarded by actuating the discarding push-button 16.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e,g, each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A system for titrating liquids, the system comprising:
a syringe (1) comprising a plunger (9) and a holding device;
a metering equipment (13) comprising:
an additional holding device for holding the syringe (1) on the holding device;
a driving device (18) having a motor (19), which is detachably coupled with the plunger (9) of the syringe (1) when the same is held by the additional holding device;
an operating device (23) for operating the metering equipment (13); and
a control device (22), connected with the operating device (23) and the driving device (18), configured to:
control a movement of the plunger (9) for the delivery of a first amount of liquid in a first delivery phase,
wherein the control device is further configured to control the movement of the plunger in the first delivery phase when an operating element of the operating device is actuated, and
wherein the control device is further configured to reduce the speed of the plunger with respect to its speed at the preceding actuation at every subsequent actuation of the operating element,
and configured to control the movement of the plunger (9) for the delivery of at least one defined second amount of liquid in a second delivery phase when triggered by an actuation of the operating device (23) or by reaching the end of the first delivery phase, wherein the at least one defined second amount of liquid is less than the first amount of liquid.

2. The system for titrating liquids of claim 1, further comprising:
at least one tag (6, 7) disposed on a flange (5) of the syringe (1),
wherein the metering equipment (13) further comprises a reading device (17) for reading the tag (6, 7) of the syringe (1).

3. A system according to claim 2, wherein the tag (6, 7) is read mechanically and/or optically by the reading device.

4. A system according to claim 2, wherein the tag (6, 7) is configured to indicate the nominal volume and/or the construction type and/or the material and/or the purity grade and/or the manufacturer and/or the manufacturing date and/or performed usages of the syringe (1).

5. A system according to claim 2, wherein the control device (22) is configured to control the movement of the plunger (9), the speed and/or acceleration of the plunger (9) and/or the displacement of the plunger (9) depending on the tag of the syringe (1).

6. A system according to claim 5, wherein the control device is configured to control a speed and/or an acceleration, and/or a displacement of the plunger (9) such that the speed, and/or the acceleration, and/or the displacement of the plunger of a syringe with a first volume is less than the speed, the acceleration, and/or the displacement of the plunger of a syringe with a second volume less than the first volume.

7. A system according to claim 5, wherein the control device (22) is configured to control a speed and/or an acceleration, and/or displacement of the plunger (9) such that the speed, the acceleration, and/or displacement of the plunger of a syringe with a first volume is greater than the speed, and/or the acceleration, and/or the displacement of the plunger of a syringe with a second volume less than the first volume.

8. A system according to claim 2, wherein the control device (18) is configured to switch into a titration mode and/or into a dispensing mode and/or into a pipetting mode and/or into an aspiration mode and/or into a sequential dispensing mode.

9. A system according to claim 1, wherein the control device (22) is configured to control the delivery of small defined amounts of liquid having a volume smaller than 1/100 of the nominal volume of the syringe (1).

10. A system according to claim 9, wherein the control device (22) is configured to control the delivery of small defined amounts of liquid having a volume smaller than 1/500 of the nominal volume of the syringe (1).

11. A system according to claim 10, wherein the control device (22) is configured to control the delivery of small defined amounts of liquid having a volume in the region of about one or several thousandths of the nominal volume of the syringe (1).

12. A system according to claim 1, wherein the control device (22) is configured to control the delivery of the second amount of liquid in the form of droplets.

13. A system according to claim 1, wherein the control device (22) is configured to control the delivery of the second amount of liquid in a free jet or in the form of ejected droplets.

14. A system according to claim 1, wherein the control device (22) is configured to control the delivery of the second amount of liquid in the form of a running off flow or running off droplets.

15. A system according to claim 1, wherein the control device (22) is configured to control a movement of the plunger (9) only for a predetermined number of actuations of the operating element, and is configured to initiate the second delivery phase.

16. A system according to claim 1, wherein the control device (22) is configured to initiate the second delivery phase upon the actuation of the operating device, wherein the actuation is a pre-defined actuation.

17. A system according to claim 1, further comprising a sensor which aims at a volume to which a delivery opening of the syringe (1) is directed when it is held by the additional holding device on the metering equipment (13), in order to detect an approach to the apex point of the titration, and the control device (22) being configured to reduce the speed of the plunger (9) and/or initiate the second delivery phase when approaching the apex point of the titration in the first delivery phase, wherein the control device is connected to the sensor.

18. A system according to claim 2, wherein the holding device comprises the flange (5) on a cylindrical or sleeve-shaped body of the syringe (1) and/or a collar at the end of the plunger (9) of the syringe (1).

19. A system according to claim 2, wherein the additional holding device comprises a plug-in receptacle (14) of the metering equipment (13) and at least one gripper, which is movable from a position releasing the holding device to a position capturing the holding device in the plug-in receptacle (14).

20. A system according to claim 2, wherein the driving device (18) comprises an electric motor (19).

21. A system according to claim 20, wherein the electric motor (19) is a DC motor.

22. A system according to claim 2, wherein the control device (22) is configured to establish the amount of liquid that has been delivered by summing the amount of liquid delivered in the first delivery phase and the second delivery phase.

23. A system according to claim 2, further comprising an increment transmitter and a sensor, wherein the driving device (18) and/or the plunger (9) is coupled with the increment transmitter for detecting the position of the plunger (9), and the control device (22) is coupled with the sensor for sensing the increment transmitter.

24. A system according to claim 2, wherein the operating device (23) comprises at least one electric push-button (23.2) and/or an electric switch.

25. A system according to claim 2, wherein the control device (22) is an electric control device.

26. A system according to claim 25, wherein the control device is program driven.

\* \* \* \* \*